US011123221B2

(12) United States Patent
Dabrowiak et al.

(10) Patent No.: US 11,123,221 B2
(45) Date of Patent: Sep. 21, 2021

(54) MANAGING PATIENT BODY TEMPERATURE USING ENDOVASCULAR HEAT EXCHANGE IN COMBINATION WITH BODY SURFACE HEAT EXCHANGE

(71) Applicant: ZOLL Circulation, Inc., San Jose, CA (US)

(72) Inventors: Jeremy Thomas Dabrowiak, Santa Clara, CA (US); Mark G Mitchell, San Jose, CA (US); James D Mazzone, San Jose, CA (US); Jeffrey R Resnick, Foster City, CA (US)

(73) Assignee: ZOLL Circulation, Inc., San Jose, CA (US)

( * ) Notice: Subject to any disclaimer, the term of this patent is extended or adjusted under 35 U.S.C. 154(b) by 332 days.

(21) Appl. No.: 15/412,390

(22) Filed: Jan. 23, 2017

(65) Prior Publication Data
US 2018/0207024 A1    Jul. 26, 2018

(51) Int. Cl.
*A61F 7/00* (2006.01)
*A61F 7/02* (2006.01)
*A61F 7/12* (2006.01)

(52) U.S. Cl.
CPC ............ *A61F 7/0085* (2013.01); *A61F 7/02* (2013.01); *A61F 7/12* (2013.01); *A61F 2007/0054* (2013.01); *A61F 2007/0055* (2013.01); *A61F 2007/0056* (2013.01); *A61F 2007/0093* (2013.01); *A61F 2007/0096* (2013.01); *A61F 2007/0295* (2013.01); *A61F 2007/0296* (2013.01); *A61F 2007/0298* (2013.01); *A61F 2007/126* (2013.01)

(58) Field of Classification Search
CPC combination set(s) only.
See application file for complete search history.

(56) References Cited

U.S. PATENT DOCUMENTS

| 4,288,205 | A | 9/1981 | Henk |
| 5,098,261 | A | 3/1992 | Bertoncini |
| 6,878,156 | B1 | 4/2005 | Noda |
| 7,070,612 | B1 | 7/2006 | Collins et al. |
| 8,475,509 | B2 | 7/2013 | Dae |
| 2004/0050154 | A1 | 3/2004 | Machold et al. |
| 2005/0096715 | A1* | 5/2005 | Magers ................ A61B 18/02 607/105 |
| 2008/0262377 | A1* | 10/2008 | Belson ................ A61F 7/0085 600/549 |
| 2010/0087900 | A1* | 4/2010 | Flint .................... A61B 5/1101 607/104 |

(Continued)

FOREIGN PATENT DOCUMENTS

| WO | WO2002/007793 A2 | 1/2002 |
| WO | WO2004/023982 A2 | 3/2004 |
| WO | WO 2013/016437 | 1/2013 |

OTHER PUBLICATIONS

PCT International Search Report dated Mar. 19, 2018 in related PCT Application No. PCT/US2018/014899.

*Primary Examiner* — Joseph A Stoklosa
*Assistant Examiner* — Adam J Avigan
(74) *Attorney, Agent, or Firm* — Fish & Richardson P.C.

(57) ABSTRACT

The present disclosure includes devices, systems and related methods useable for controlling a patient's body temperature by endovascular heat exchange as well as body surface heat exchange.

21 Claims, 5 Drawing Sheets

(56) References Cited

U.S. PATENT DOCUMENTS

| | | | |
|---|---|---|---|
| 2011/0137249 A1* | 6/2011 | Collins | A61F 7/12 |
| | | | 604/113 |
| 2014/0135879 A1 | 5/2014 | Flint | |
| 2015/0223972 A1* | 8/2015 | Dabrowiak | A61F 7/0085 |
| | | | 607/106 |
| 2015/0272513 A1 | 10/2015 | Tan et al. | |
| 2016/0058613 A1* | 3/2016 | Palazzolo | A61N 2/006 |
| | | | 607/105 |
| 2016/0287434 A1* | 10/2016 | Dabrowiak | A61F 7/0085 |
| 2017/0224528 A1* | 8/2017 | Berg | A61F 7/02 |

\* cited by examiner

MANAGING PATIENT BODY TEMPERATURE USING ENDOVASCULAR HEAT EXCHANGE IN COMBINATION WITH BODY SURFACE HEAT EXCHANGE

FIELD OF THE INVENTION

The present disclosure relates generally to the fields of medicine and biomedical engineering and more particularly to devices, systems and related methods useable for controlling a patient's body temperature by endovascular heat exchange as well as body surface heat exchange.

BACKGROUND

Pursuant to 37 CFR 1.71(e), this patent document contains material which is subject to copyright protection and the owner of this patent document reserves all copyright rights whatsoever.

Various devices and methods for altering or maintaining the body temperature of a patient exist. These include endovascular systems wherein heat exchange catheters are inserted into a patient's blood vessel and used to warm or cool the patient's flowing blood as well as body surface heat exchange systems wherein heat exchange pads, garments or blankets are used to non-invasively warm or cool the patient's body.

Examples of commercialized endovascular heat exchange systems include the Thermogard XP Temperature Management System (ZOLL Circulation, Inc., San Jose, Calif.) and InnerCool RTx Endovascular Temperature Modulation System (ZOLL Circulation, Inc., San Jose, Calif.). Examples of body surface heat exchange systems include the STx Surface Pad System (ZOLL Circulation, Inc., San Jose, Calif.), the ARCTIC SUN 5000 Temperature Management System (Bard Medical Division, Covington, Ga.), the Criticool System (MTRE Advanced Technologies, Ltd., Feasterville-Trevose, Pa.) and the BAIR HUGGER, BAIR PAWS and POLAR AIR Systems (3M, St. Paul, Minn.).

SUMMARY

In accordance with the present disclosure, there are provided devices and systems useable for endovascular and body surface heat exchange and related methods for using such devices and systems.

The present disclosure describes systems and methods useable for endovascular and/or body surface heat exchange as well as new clinical treatment methods for advantageously utilizing such dual capability for endovascular and/or body surface heat exchange.

In accordance with one embodiment, there are provided devices, systems and methods for controlling body temperature of a subject wherein a system comprises: (a) an endovascular heat exchange device (e.g., a heat exchange catheter), (b) a body surface heat exchange device (e.g., pad(s), blanket(s), garment(s), etc.), (c) at least one source of heat exchange fluid(s); (d) at least one heater/cooler, (e) at least one pumping apparatus and (f) at least one controller programmed to control operation of the system in alternate modes. The alternate modes may comprise 1) a first mode wherein heated or cooled heat exchange fluid is circulated through only the endovascular heat exchange device, 2) a second mode wherein heated or cooled heat exchange fluid is circulated through only said at least one body surface heat exchange device and 3) a third mode wherein heated or cooled heat exchange fluid is circulated through both the endovascular heat exchange device and the body surface heat exchange device. The controller may include a user interface (e.g., a touch screen display) which is useable to select the mode in which the system is to be operated. Optionally, when Mode 3 is selected, the controller may be further programmed to permit or prompt the use to select from a plurality of sub-modes in which the endovascular and body surface heat exchange devices are operable. Such sub-modes may comprise i) a first sub-mode wherein the endovascular heat exchange device and the body surface heat exchange device simultaneously cool or warm; ii) a second sub-mode wherein one of the endovascular heat exchange device and the body surface heat exchange device cools while the other of the endovascular heat exchange device and the body surface heat exchange device warms. In at least some embodiments, the selectable sub-modes may further comprise iii) a third sub-mode wherein, for an initial period, the endovascular heat exchange device and the body surface heat exchange device simultaneously cool or warm and, for a subsequent period, one of the endovascular heat exchange device and the body surface heat exchange device cools while the other of the endovascular heat exchange device and the body surface heat exchange device warms. This third sub-mode, when and if operational, may in some cases, be employed to initially cause both the endovascular heat exchange device and the body surface heat exchange device to begin lowering of a subject's body temperature and, at a desired time, switch the body surface heat exchange device to a warming mode to apply warming to the subject's body surface (e.g., for comfort or deterrence of shivering) while causing the endovascular heat exchange device to continue lowering the subject's core body temperature to an intended hypothermic target temperature.

In accordance with another embodiment, there is provided a kit for enabling surface cooling which comprises a) a source of heat exchange fluid, b) a heater/cooler, c) pumping apparatus and d) a programmable controller for circulating heated or cooled heat exchange fluid through an endovascular heat exchanger to a system that is useable for circulating heated or cooled heat exchange fluid through a body surface heat exchanger. Such kit may comprise at least a second source of heat exchange fluid, a second pumping apparatus useable for circulating fluid through body surface heat exchange device(s) and a storage medium containing code for reprogramming the system's programmable controller such that it will additionally control the kit's pumping apparatus and potentially other components that participate in circulation of temperature-controlled heat exchange fluid through added body surface heat exchange device(s). In some embodiments, the kit may additionally include body surface heat exchange device(s) through which the kit's second pumping apparatus will circulate the temperature-controlled heat exchange fluid. In some embodiments, the kit may also include a second heater/cooler to augment the system's heater/cooler in providing sufficient temperature-controlled heat exchange fluid for circulation through the body surface heat exchange device(s).

Further, there are provided systems and methods wherein energy that is produced by a heater/cooler of an endovascular heat exchange system (e.g., exhausted heat) is used directly or indirectly for circulation of warm or cool heat exchange fluid (e.g., gas or liquid) through body surface heat exchange device(s). In some embodiments, warm air that is exhausted from a heater/cooler condenser or other component of the endovascular heat exchange system may be captured and channeled through a warm-air blanket or other body surface heat exchange device which utilizes a flow of warm air. In other embodiments such exhausted warm air may be captured and channeled through a gas/liquid heat exchanger to warm a suitable liquid which is in turn circulated through a body surface heat exchanger of a type which utilizes a flow of warm liquid.

Still further aspects and details of the present invention will be understood upon reading of the detailed description and examples set forth herebelow.

BRIEF DESCRIPTION OF THE DRAWINGS

FIGS. 8A through 8C are partial cross-sectional views of the pump raceway and tubing components of certain embodiments of peristaltic pumps. Specifically. FIG. 7C shows a peristaltic pump which has a single raceway within which one or more tubes are positioned to allow for variable compression of tube(s).

FIGS. 9A and 9B show cross-sectional views of peristaltic pump tubes having multiple lumens. Specifically, FIG. 9A shows a tube having two lumens and FIG. 9B shows a tube having four lumens.

DETAILED DESCRIPTION

The following detailed description and the accompanying drawings to which it refers are intended to describe some, but not necessarily all, examples or embodiments of the invention. The described embodiments are to be considered in all respects only as illustrative and not restrictive. The contents of this detailed description and the accompanying drawings do not limit the scope of the invention in any way.

Figure 1:
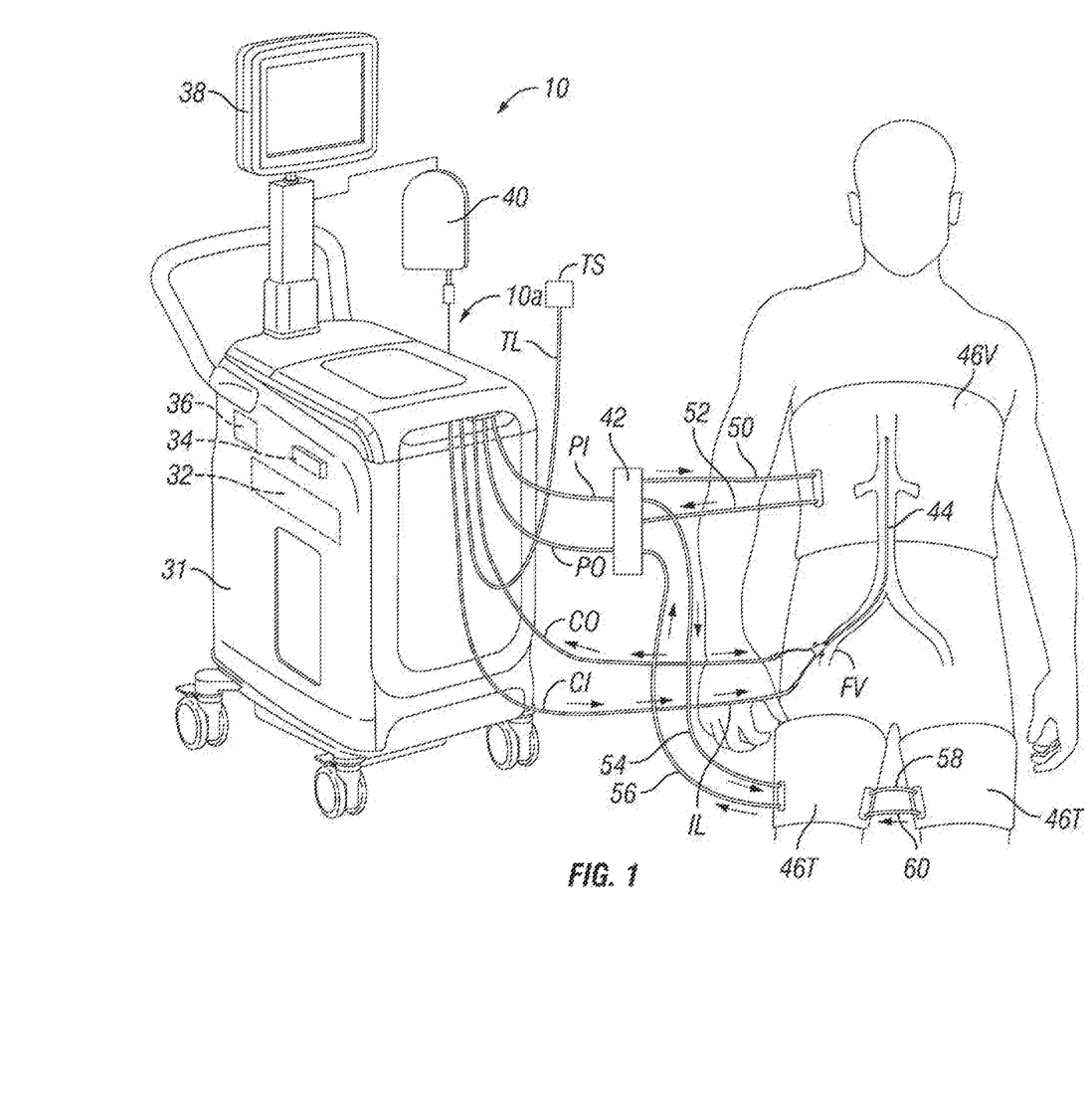
FIG. 1 generally shows a body temperature management system which comprises a control console, endovascular heat exchange catheter and body surface heat exchange apparatus.

FIG. 1 shows a body temperature management system 10 which generally includes a control console 10a which is useable to control both an endovascular heat exchange catheter 44 and a body surface heat exchange apparatus which, in this non-limiting example, comprises a heat exchange vest 46v and a set of heat exchange thigh pads 46t.

The control console 10a comprises a housing 30 within which, or on which, there are positioned heating/cooling apparatus 32 for alternately heating and cooling a heat exchange fluid, at least one pump 34 for pumping the heat exchange fluid and a programmable controller 36. A user interface 38, such as a liquid crystal display (LCD), is in communication with the controller 36. The user interface displays system information and also receives user input and displays information, as described more fully herein.

At least one reservoir or source of heat exchange fluid 40 is connected by tubing to the heater/cooler 32. Typically, heat exchange fluid for circulation through the heat exchange catheter 44 will comprise sterile 0.9% NaCl solution and the heat exchange fluid for circulation through the body surface heat exchange apparatus 46v, 46t may comprise non-sterile water or any other suitable fluid. In some embodiments, a common heat exchange fluid (e.g., sterile 0.9% NaCl solution) may be circulated through both the endovascular heat exchange catheter 44 and the body surface heat exchange apparatus 46v, 46t.

At least one body temperature sensor TS is connected, by way of a temperature lead TL or alternatively by wireless connectivity, to the controller 36. This body temperature sensor TS may be positioned at any suitable location on or in the patient's body to monitor body temperature. In some embodiments, a plurality of temperature sensors TS may be employed. In some embodiments the temperature sensor TS may be positioned on or in the heat exchange catheter 10b or may be inserted through a lumen of the heat exchange catheter 10b. In other examples, the temperature sensor TS may be positioned elsewhere in or on the patient's body, such as on the patient's skin (e.g., axillary temperature sensor) or in the patient's vasculature, esophagus, rectum, bladder, ear canal or other suitable location.

The heater/cooler 32 may in some embodiments comprise common apparatus useable for heating/cooling heat exchange fluid for circulation through the catheter 44 as well as heat exchange fluid for circulation through the body surface heat exchange apparatus 46x, 46t. In other embodiments the heater/cooler 32 may comprise separate heater/cooler apparatus, e.g., one for heating/cooling heat exchange fluid for circulation through the catheter 44 and one for heating/cooling heat exchange fluid for circulation through the body surface heat exchange apparatus 46v, 46t. In certain embodiments, the heater/cooler or heating/cooling apparatus may include a refrigerant circuit including heat exchange plates having chambers through which refrigerant and/or other fluids flow. The heat exchange plates may be configured to receive a heat exchange cassette through which heat exchange fluid flows, such that the refrigerant, other fluid, e.g., water, and/or the heat exchange fluid are in thermal contact with each other to facilitate heat exchange between the fluids. In other embodiments, the heater/cooler or heating/cooling apparatus may include a refrigerant circuit, cold well, and/or heat exchange coil, which may be positionable within the cold well.

In the non-limiting example of FIG. 1, the endovascular heat exchange catheter 44 is connected to a catheter inflow line CI through which temperature controlled heat exchange fluid circulates from the heater/cooler 32 into the catheter 44 and a catheter outflow line CO through which heat exchange fluid circulates from the catheter 44 back into the heater cooler 32. The body surface heat exchange apparatus 46v, 46t is connected to a surface or surface pad inflow line PL and a surface or surface pad outflow line PO. In the specific example shown, the surface pad inflow line PL and a surface pad outflow line PO are connected to a manifold 42 or other flow dividing apparatus. A portion of the heat exchange fluid from the surface pad inflow line PI is channeled by manifold 42 to vest 46v through line 50. Returning heat exchange fluid then flows back to the manifold 42 from the vest 46v through return line 52. The thigh pads 46t are interconnected by tubes 58, 60 to facilitate circulation of heat exchange fluid through both thigh pads 46t. Temperature controlled heat exchange fluid that enters the manifold 42 from surface pad inflow line PI then circulates from the manifold 42 through lines 54 and 58 and through the thigh pads 46t. Spent heat exchange fluid then returns from the thigh pads 46t, through lines 56 and 60, to manifold 42. The manifold 42 combines the flows of returning heat exchange fluid from lines 52 and 56 and circulates such combined fluid back to the heater/cooler 32 through surface pad outflow line PO.

The control console 10a may, in some embodiments, be programmed and equipped with components for alternate operation in either an IVTM (intra-vascular) mode wherein heat exchange fluid is circulated through the heat exchange catheter 44 or a SURFACE mode wherein heat exchange fluid is circulated through the body surface heat exchange apparatus 46v, 46t. In other embodiments, the control console 10a may be programmed and equipped to operate not only in the IVTM mode or SURFACE mode, but additionally in a third IVTM+SURFACE mode wherein heat exchange fluid is circulated simultaneously through the heat exchange catheter 44 as well as the body surface heat exchange apparatus 46v, 46t. As explained more fully below, in some applications of IVTM+SURFACE mode, both the endovascular heat exchange catheter 44 and the body surface heat exchange apparatus 46v, 46t may simultaneously warm or simultaneously cool the subject's body. In other applications of IVTM+SURFACE mode, one of the endovascular heat exchange catheter 44 and the body surface heat exchange apparatus 46v, 46t may be warming while the other is cooling. For example, in applications where it is desired to rapidly induce hypothermia in a subject, the system may be operated in IVTM+SURFACE mode with both the endovascular heat exchange catheter 44 and the body surface heat exchange apparatus 46v, 46t cooling the subject so as to lower the subject's core body temperature as rapidly as possible. In applications where it is desired to maintain mild hypothermia while providing some comfort to the subject, the system may be operated in IVTM+SURFACE mode with the endovascular heat exchange catheter 44 operating mainly in cooling mode to maintain the hypothermic core body temperature while the body surface heat exchange apparatus 46v, 46t operates in a warming mode to warm the subject's body surface. In applications where it is desired to rapidly induce hypothermia while deterring or delaying shivering, the system may be operated in IVTM+SURFACE mode with both the endovascular heat exchange catheter 44 and the body surface heat exchange apparatus 46v, 46t cooling the subject for an initial period of time. Then, upon reaching a point in the procedure where shivering is imminent or likely, the body surface heat exchange apparatus 46v, 46t may switch from cooling to warming while the endovascular heat exchange catheter 44 continues to cool the subject's body core. Such warming of the subject's body surface may deter or minimize a shivering response as the subject's core temperature continues to lower to the hypothermic target temperature.

Figure 2:
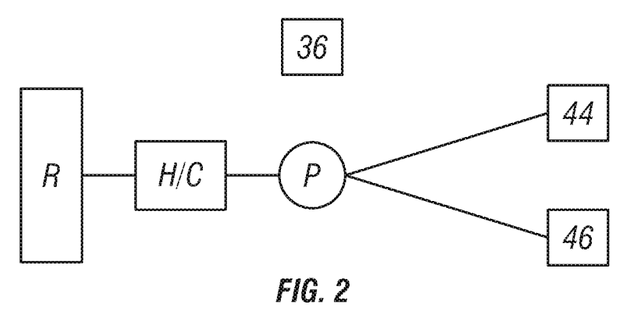
FIG. 2 is a schematic diagram showing certain components of one embodiment of a body temperature management system of the type generally shown in FIG. 1.

FIGS. 2 through 6B are schematic diagrams which show examples of ways in which certain components of the system 10 may be configured. Specifically, FIG. 2 shows an embodiment in which a common reservoir R, common heater/cooler apparatus H/C and common pump P are controlled by controller 36 to separately or simultaneously circulate heat exchange fluid through a heat exchange catheter 44 and/or body surface heat exchanger 46. In such embodiment, the reservoir R contains a sufficient amount of a single heat exchange fluid for circulation through the heat exchange catheter 44 and/or the body surface heat exchanger 46. The heater/cooler H/C has variable capacity for heating/cooling varying volumes of the heat exchange fluid as needed for circulation through the heat exchange catheter 44 and/or the body surface heat exchanger 46. Also, the pump P is a variable throughput pump useable for pumping varying volumes of the heat exchange fluid at varying volume flow rates as needed for circulation through the heat exchange catheter 44 and/or the body surface heat exchanger 46.

Figure 3:
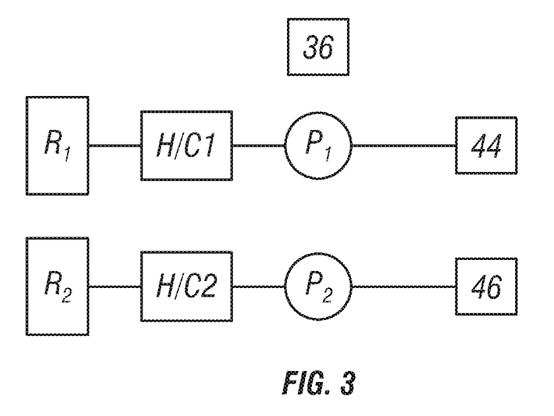
FIG. 3 is a schematic diagram showing certain components of another embodiment of a body temperature management system of the type generally shown in FIG. 1.

FIG. 3 diagrams an embodiment wherein one or more controller(s) 36 is/are programmed to control the operation of two discrete circuits. In one circuit, a first reservoir R1, first heater/cooler H/C1 and first pump P1 circulate a heat exchange fluid through the heat exchange catheter 44. In the other circuit, a second reservoir R2, second heater/cooler H/C2 and second pump P2 circulate the same or different heat exchange fluid through the body surface heat exchanger 46. Both circuits may be located on or in a single console 31. The ability to control each circuit may be independent of one another. For example, while the first circuit is causing the heat exchange catheter to cool the subject's core the second circuit may be operating to warm the subject's body surface or vice versa.

Figure 4:
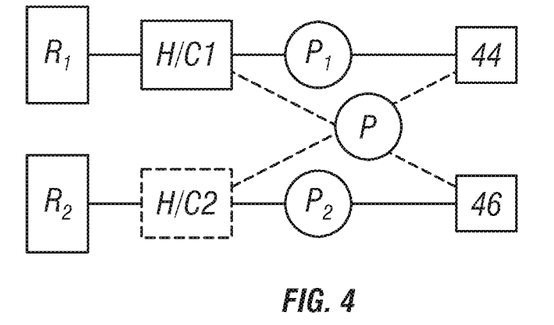
FIG. 4 is a schematic diagram showing certain components of yet another embodiment of a body temperature management system of the type generally shown in FIG. 1.

FIG. 4 illustrates a hybrid example which includes separate discrete first and second circuits as shown in FIG. 3 as well as an alternative common pump P and the controller 36 is programmed to alternately operate the circuits separately or in a combined mode. For example, the first heater/cooler H/C1 could be for only cooling and the second heater cooler H/C2 could be for only warming. When the system is operating in a mode where both the heat exchange catheter 44 and body surface heat exchanger 46 are being used to cool the body, the controller 36 may cause cooled heat exchange fluid from the first heater/cooler H/C1 to be pumped by common pump P through both the heat exchange catheter 44 and body surface heat exchanger 46. Alternatively, when the system is operating in a mode where the heat exchange catheter 44 is cooling the subject's body core while the body surface heat exchanger 46 is warming the subject's skin, the controller 36 may cause fluid from first reservoir R1 to be cooled by first heater/cooler H/C1 and pumped by the first pump P1 through the heat exchange catheter 44. At the same time, the controller 36 may cause fluid from the second reservoir R2 to be warmed by the second heater/cooler H/C2 and circulated by second pump P2 through the body surface heat exchanger 46. Although FIG. 4 shows separate first and second reservoirs R1, R2, a single reservoir R containing a common heat exchange fluid could alternatively be used.

Figure 5:
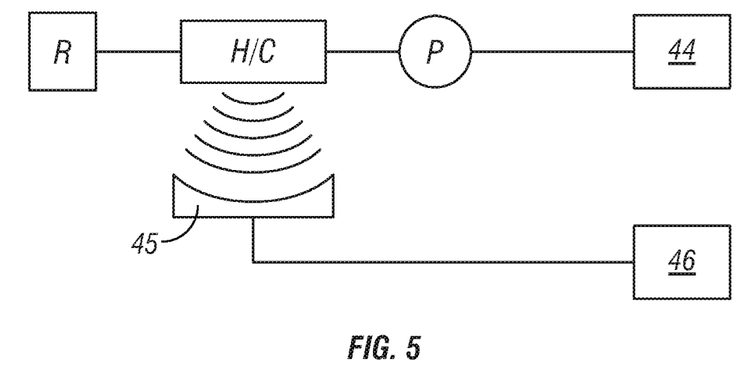
FIG. 5 is a schematic diagram showing certain components of still another embodiment of a body temperature management system of the type generally shown in FIG. 1.

FIG. 5 shows another embodiment wherein a primary heat exchange circuit having a reservoir R, heater/cooler H/C and pump P circulates warmed or cooled heat exchange fluid through a heat exchange catheter 44 and exhausted heat or other energy emitted from the heater/cooler H/C is captured and/or otherwise used by an energy capturing/converting apparatus 45 to provide a flow of temperature controlled heat exchange fluid (liquid or gas) to the body surface heat exchanger 46. The energy capturing/converting apparatus 45 may comprise a gas-liquid heat exchanger in which warm air exhausted from a condenser of the heater/cooler H/C is used to warm a heat exchange liquid which is then circulated, by way of a second pump (not shown), through the body surface heat exchanger 46. Alternatively, the energy capturing/converting apparatus 45 could be a shroud, duct or other air capturing/channeling apparatus that would capture warm air exhausted from the heater/cooler H/C and circulate it through a warm air type of body surface heat exchanger (e.g., a Bair Hugger blanket or Bair Paw garment). In some embodiments the heater/cooler H/C may comprise a radiator style heat exchanger, e.g., a metal heat exchanger, where air from a condenser can blow over adjacent channels or chambers in cold plates or a cold well holding saline, water or other fluid for a body surface heat exchanger. The fluids may be isolated but in adjacent chambers such that heat transfer between the chambers occurs. The chambers may be convoluted or have several fins to increase surface area and heat exchange between fluids, e.g., between saline and glycol or refrigerant, similar to a radiator.

To add improved control of the fluid or water temperature for a surface system, water or other fluid flowing through the heater/cooler could be on a controlled valve to potentially mix with the water or other fluid coming from the heat transfer surface system until the desired temperature is achieved for flow through the body surface heat exchanger, e.g., surface pads. The surface system plumbing, through which water or other fluid would flow, can be heated by condenser air (as discussed above) or simply by heaters. To fine tune or adjust the temperature, water or other fluid flowing through chambers in the cold plate or heat exchanger of the heater/cooler could be mixed with, or placed in heat exchange contact with the water or other fluid from the surface system, to adjust the surface pad water/fluid temp (e.g., cool it). A valve may be used to control mixing or contact between the two fluids.

Figure 6A:
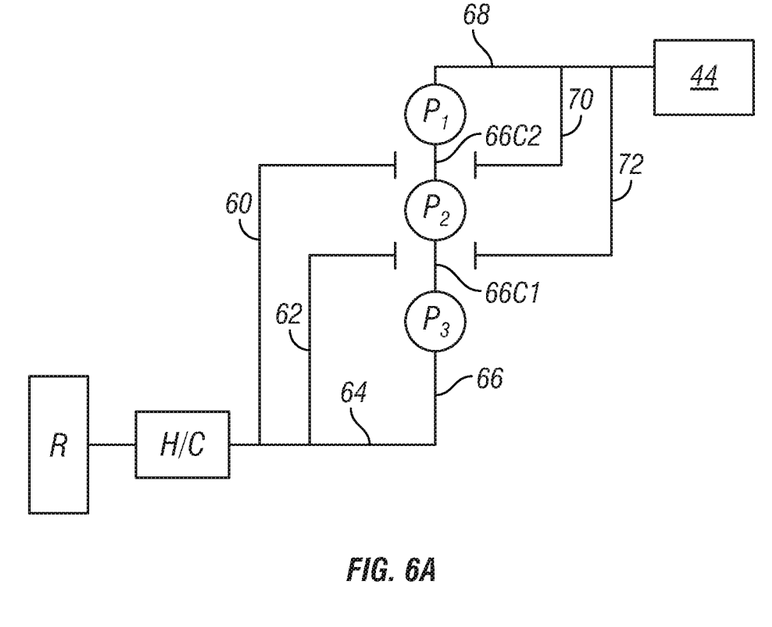
FIGS. 6A and 6B are schematic diagrams showing certain components of another embodiment of a body temperature management system.
Figure 6B:
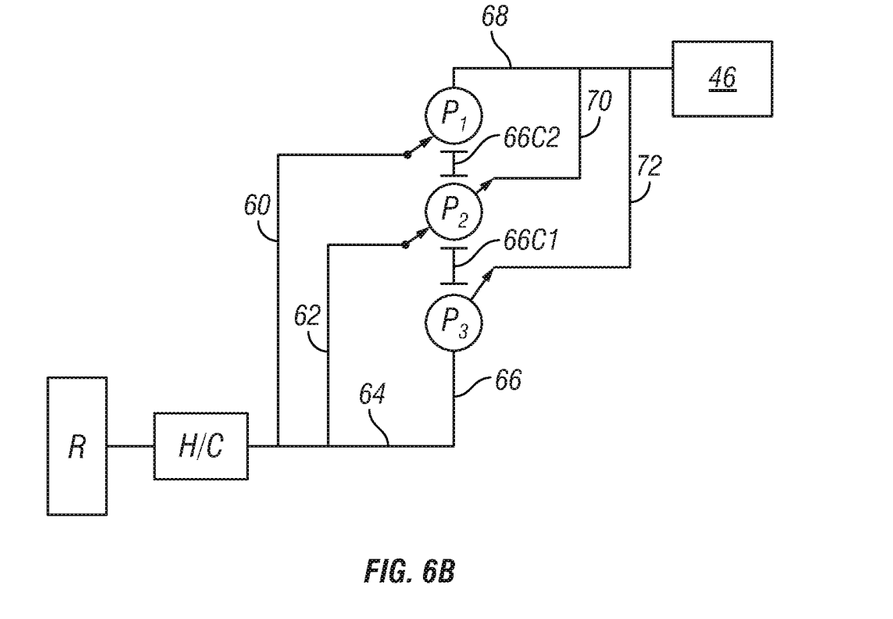

FIGS. 6A and 6B show a schematic diagram of a system wherein a plurality of pumps P1, P2, P3 may alternately be operated in series (FIG. 6a) to provide an increase in fluid pressure to optimize a temperature management system when the system has a higher resistance to fluid flow, i.e., when the system is circulating fluid through a heat exchange catheter 44 or in parallel (FIG. 6B) to provide an increase in volume flow rate to optimize a temperature management system when the system has a lower resistance to fluid flow and requires a higher volume flow rate, i.e., when the system is circulating fluid through a body surface heat exchanger 46.

The system in FIGS. 6A and 6B includes pumps P1, P2 and P3. Although this example shows three pumps, any desired number of 2 or more pumps may be used. Depending on the arrangement and position of tubing lines or segments, valves or clamps, which control fluid flow through the tubing lines or segments and pumps within the system, the fluid pressure, flow velocity and/or volume flow rate in the system may be altered. For example, FIG. 6A shows three pumps P1, P2 and P3 in the system connected by tubing segments 66, 66C1, and 66C2, through which fluid flows into endovascular heat exchange catheter 44. When valves and tubing segments are positioned as shown in FIG. 6A, the pumps are connected in series, providing a higher fluid pressure through the system than if the pumps were connected in parallel.

When the valves and tubing segments are positioned as shown in Figure GB, tubing segments 66, 66C1, and 66C2 are decoupled from pumps P1, P2 and P3, and the pumps are connected in parallel, providing a higher volume flow rate through the system than if the pumps were arranged in series. When the pumps are connected in parallel, fluid flows from tubing 60 through pump P1 then onto body surface heat exchange device 46, from tubing 62 through P2 then onto body surface heat exchange device 46 via tubing 70, and from tubing 64 through P3 then onto body surface heat exchange device 46 via tubing 72.

Therefore, the system can support either an endovascular heat exchange catheter 44 by opening or closing the valves and/or tubing lines/segments such that the pressure across the pumps is added, or a body surface heat exchange device 46 by opening or closing valves and/or tubing lines/segments such that volume flow through the pumps is added. The valves, tubing lines/segments and/or clamps may be manipulated, e.g., using a controller programmed to control operation of the system, depending on whether endovascular heat exchange and/or surface heat exchange is desired, allowing a user to switch between the two modes of heat exchange.

More specifically, in the non-limiting example of FIG. 6a, valves are positioned to close lines 60, 62, 70 and 72 such that heat exchange fluid flows from reservoir R, through heater/cooler HO, through lines 64 and 66, through pump P3, through line 66C1, through pump P2, through line 66C2, through pump P1, through line 68 and to the endovascular heat exchanger 44. In the non-limiting example of FIG. 6B, valves are positioned to open lines 60, 62, 70 and 72 such that heat exchange fluid flows from reservoir R, through heater/cooler HC and through each of lines 60, 62 and 64. Fluid from line 60 is pumped by pump P1 into line 68, fluid from line 62 is pumped by pump P2 into line 70 and fluid from line 64 flows through line 66 and is pumped by pump P3 into line 72. Fluid from each of lines 70 and 72 enter line 68 in combination with the fluid that has been piped into line 68 by pump P1, and all of the fluid then flows through the body surface heat exchanger 46.

In an alternative embodiment, P1 may pump fluid through a first line to an endovascular catheter, while P2 and P3 (arranged in parallel) may pump fluid through a second line to a body surface heat exchanger. When separate lines for endovascular and body surface heat exchangers are utilized, a single system may operate both endovascular and body surface heat exchangers simultaneously where each line is coupled to one or more pumps arranged to optimize fluid circulation through either an endovascular or body surface heat exchanger.

Figure 7:
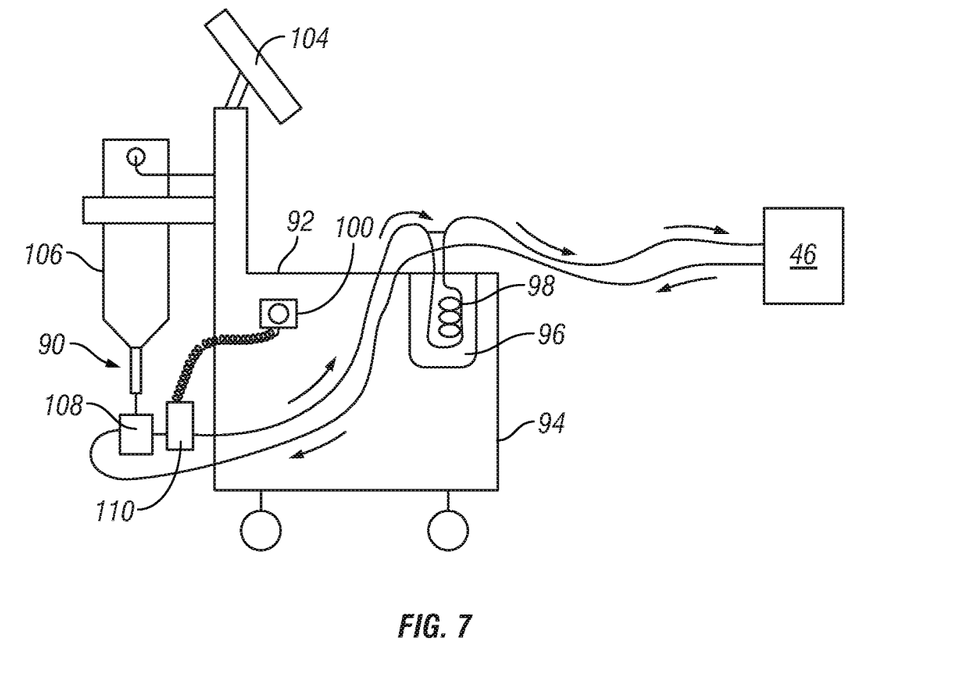
FIG. 7 is a diagram of an endovascular temperature management system equipped with add-on components to render it capable of operating body surface heat exchange apparatus as an alternative to endovascular heat exchange apparatus.

FIG. 7 shows an endovascular heat exchange system control console 92 that has been equipped with a surface cooling kit. The surface cooling kit, which may be fully or partially disposable, additionally renders this console 92 capable of controlling a body surface heat exchange device 46 instead of or in addition to an endovascular heat exchange catheter.

In the console 92 depicted in this example, the circulating heat exchange fluid is warmed or cooled by a circulation coil 98 or other heat exchanger that is submersed within a well 96 that contains warmed or cooled fluid (e.g., a "cold well"). A system of his type is commercially available as the Thermogard XP System (ZOLL Circulation, Inc.). In other embodiments, the surface cooling kit may be modified to include another type of cooling/warming component or heat exchanger instead of the coil to render it useable with other types of endovascular heat exchange system consoles. For example, the surface cooling kit may also be useable with other consoles, where the kit includes different cooling/warming components and/or heat exchangers, such as a cassette through which a working fluid, e.g., saline flows. The cassette can be positioned between cold plates through which a coolant or refrigerant may flow, such that the refrigerant or coolant comes into thermal contact with the working fluid. In this example, the surface cooling kit includes a reservoir 106, a pump 110, a coil 98, associated tubing and a software modification. Optionally, the kit may also include an air trap 108. Also optionally, the kit may include an air separator (not shown) to prevent air from entering the pump 110 or a dual lumen IV spike similar to that included in the commercially available Thermogard XP Start Up Kit (ZOLL Circulation, Inc., San Jose, Calif.) and that shown in U.S. Pat. No. 6,878,156 (Noda) entitled Portable Cooler For Heat Exchange Catheter, the entire disclosure of which is expressly incorporated herein by reference. Such dual lumen IV spike will cause air to collect at the top of the reservoir 106 as the liquid level in the reservoir lowers.

Typically, the volume of fluid required for priming and operation of a body surface heat exchange device is much greater than the volume required for priming and operation of a heat exchange catheter. Thus, the reservoir 106 may be an appropriately sized bag (e.g., a 2 liter IV bag) or other vessel that is pre-filled or finable with heat exchange fluid (e.g., water, saline or other suitable liquid) in an amount sufficient to prime and operate the intended body surface heat exchange device(s) 46.

The pump 110 may be a peristaltic roller pump, centrifugal pump, screw pump, gear pump, or diaphragm pump or other suitable pump. In this example, the pump 110 is connected to a power outlet 100 on the console 94. The pump 110 may have an integrated motor which, along with the pump 110, may be disposable. Alternatively, the pump 110 may be powered by a separate motor, which could be of a reusable type.

The software modification will program or reprogram the console's existing controller 36 to facilitate operation of the system in either endovascular heat exchange mode or a body surface heat exchange mode.

After the software modification, upon powering on the system, the controller 36 may prompt the user to select, via user interface 104, either SURFACE mode or IVTM (intravascular) mode. Alternately the controller 36 may be programmed to detect whether the pump 110 or other component of the surface cooling kit has been connected to the system and, on that basis, automatically set or suggest the appropriate mode setting. Additionally, in some embodiments, software modification may provide for selection and operation of a third mode wherein both SURFACE and IVTM modes operate simultaneously as described in this application.

Once SURFACE mode has been selected, the pump within the console 92 typically used for catheter-based heat exchange will no longer turn. Instead the pump 110 of the surface cooling kit would be used.

In some embodiments, before commencing the selected mode of heat exchange, the controller 36 may prompt a user to initialize a primary or initial set up mode for priming and removal of air from the system. Alternately the system may self-prime during the normal course of use. If the optional air-trap 108 is used, this is unlikely to be feasible. Once the system is primed with heat exchange fluid, it could be used to manage patient temperature in essentially the same manner as it would typically do when performing endovascular heat exchange through a catheter (i.e., regulating the temperature of the fluid in the well 96 or in or between cold plates to alter the rate of heat transfer to-from the patient. The control algorithm may be adjusted to satisfactorily control the patient's temperature. (e.g. PID parameters)

Thus, the use of this surface cooling kit may enable an existing or newly designed endovascular heat exchange system so that it may alternatively be used for body surface heat exchange. Hardware modifications to the original system would be limited. Moreover, the water in the system would be single use and therefore much cleaner than a competitive system. In other embodiments, for example, an existing or newly designed surface cooling system could use this kit, e.g., to provide an alternate treatment pathway which uses, e.g., sterile water as the working fluid within the surface pads. This may be of benefit during situations where the treatment providers are particularly concerned about patient infection.

Figure 8A:
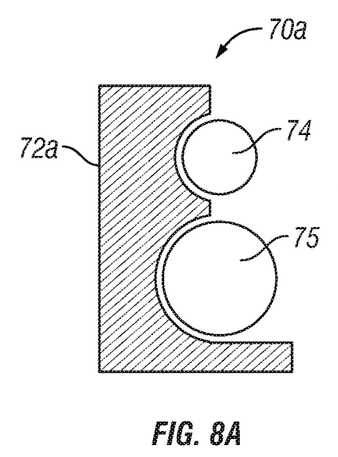
FIG. 8A shows a peristaltic pump having a first raceway with tubing of a first size for pumping heat exchange fluid through an endovascular heat exchange catheter and a second raceway with tubing of a second size for pumping heat exchange fluid through body surface heat exchange apparatus.
Figure 8B:
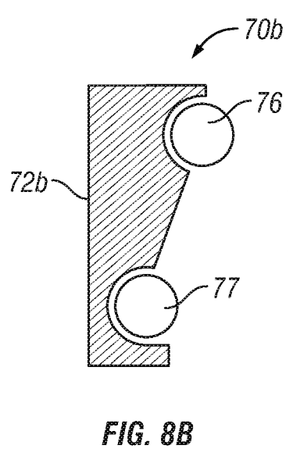
FIG. 8B shows a peristaltic pump which has first and second raceways with different sized tubes therein to allow for variable compression of the different sized tubes.
Figure 8C:
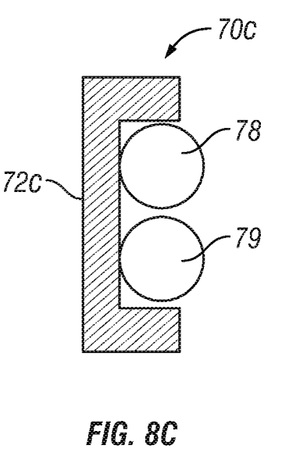

As explained above, some of the systems described herein may incorporate multichannel or variable throughput pumps that are capable of pumping heat exchange fluid(s) at either or both of 1) a relatively high fluid pressure and high flow velocity for circulation through an endovascular heat exchange catheter and/or b) a lower fluid pressure and a relatively high volume flow rate for circulation through body surface heat exchange device(s). In this regard, FIGS. 8A through 8C show partial cross-sectional views of pump raceways and tubing components of certain embodiments of peristaltic pumps. Specifically, FIG. 8A shows a peristaltic pump 70a having a raceway 72a with a first groove and tubing of a first size 74 for pumping heat exchange fluid through an endovascular heat exchange catheter and a second grove and tubing of a second size 75 for pumping heat exchange fluid through a body surface heat exchange apparatus. FIG. 8B shows a peristaltic pump 70b having a sloped raceway 72b with a first groove and tubing 76 and a second groove and tubing 77 wherein the tubing 76 and 77 may be of the same or differing sizes and wherein the pump is adapted for variable compression of the tubes. FIG. 8C shows a peristaltic pump 70c which has a raceway 72c with a single groove in which multiple tubes 78, 79 are positioned.

In the embodiment of FIG. 8A, variable compression and/or fluid pressure and volume flow rate are achieved due to the different size tubing that is utilized. The larger diameter tubing 75 will hold a larger volume of fluid than the smaller diameter tubing 74, Compression of the smaller tubing 74 will result in higher fluid pressure and higher flow velocity (to optimize circulation of fluid through an endovascular catheter) than compression of the larger diameter tubing 75. Compression of the larger diameter tubing 75 will result in a lower fluid pressure and lower flow velocity, but a higher volume flow rate (to optimize circulation of fluid through a body surface heat exchanger) than compression of the smaller diameter tubing 74. In FIG. 8B, the raceways are offset and/or have different diameters and the tubing 76 and 77 have the same diameter, so a pump roller will compress one tubing to a greater degree than the other tubing, resulting in a differentiation in fluid pressure, flow velocity and/or volume flow rate in one tubing compared to the other. For example, tubing 76 would be compressed to a greater degree than tubing 77, resulting in higher fluid pressure and flow velocity in tubing 76 than in tubing 77 (to optimize circulation of fluid through an endovascular catheter coupled to tubing 76). While tubing 76 and 77 have generally the same diameter, different sized tubing may be used to further affect the fluid in the respective tubing. In FIG. 8C, two tubes, tubing 78 and 79, are positioned within a single raceway. As a result, twice as much fluid volume and a higher volume flow rate is achieved using the same pump roller contact than would otherwise be achieved using a single tube.

The raceway and tubing embodiments described above may be used with a pump having one or more rotors with rollers, and having symmetrical or nonsymmetrical rollers. For example, a nonsymmetrical roller may include one end having a larger diameter than the other end, thereby making it capable of effecting variable compression of two different tubes (whether the tubes are the same size or differ in size) depending on which end of the roller contacts a particular tube. This may result in a differentiation in fluid pressure, flow velocity and/or volume flow rate in one tube compared to the other tube.

Figure 9A:
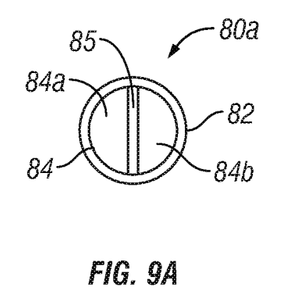
Figure 9B:
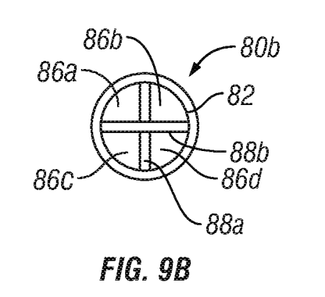

FIGS. 9A and 9B show cross-sectional views of peristaltic pump tubes 80a and 80b having multiple lumens. Specifically, FIG. 9A shows a tube 80a having two lumens 84a and 84b separated by an extrusion wall or other bulkhead 85. FIG. 9B shows a tube 80b having four lumens 86a-86d separated by crossed extrusion walls or bulkheads 88. Tube 80a or tube 80b may be used in a temperature management system capable of performing endovascular and/or surface heat exchange, as described herein, where a single tube can supply fluid for both endovascular and surface heat exchange. For example, in tube 80a, fluid for endovascular heat exchange may flow through lumen 84a and fluid for surface heat exchange may flow through lumen 84b. The tube 80a may be positioned in the raceway of a pump such that the pump rollers compress lumen 84a to a greater degree than lumen 84b, resulting in higher fluid pressure and a higher flow velocity of the fluid that flows through lumen 84a, which is supplied to a catheter, and lower fluid pressure and lower flow velocity of the fluid that flows through lumen 84b, which is supplied to a surface heat exchange device or pad. In another example, in tube 80b, fluid for endovascular heat exchange may flow through lumen 86a and fluid for surface heat exchange may flow through lumens 86b-86d, providing a larger volume of fluid and higher volume flow rate supplied to the surface heat exchange device. The tube 80b may also be positioned in the raceway of a pump such that the pump rollers compress lumen 86a to a greater degree than lumens 86b-86d, resulting in higher fluid pressure and a higher flow velocity of the fluid that flows through lumen 86a, which is supplied to a catheter, and lower fluid pressure and lower flow velocity of fluid that flows through lumens 86b-86d, which is supplied to a surface heat exchange device. In other embodiments, tubes may include two or more lumens, and each lumen may vary in size/diameter or two or more lumens may be identical in size/diameter.

The devices and systems of the present invention provide for advanced body temperature control using combination(s) of endovascular heat exchange and body surface heat exchange. The following are non-limiting examples of just a few of the various potential clinical applications of the systems described in this patent application.

Example 1

Induction and Maintenance of Hypothermia by Simultaneous Endovascular and Body Surface Heat Exchange In this example, a heat exchange system as described herein is used to attain and maintain a lowered body temperature in a human or other mammalian animal subject. A heat exchange catheter is inserted into the subject's vasculature (e.g., into the inferior vena cava or other suitable blood vessel) and one or more body surface heat exchange device(s) is/are positioned on one or more body surface(s) of the subject. A body temperature sensor is placed on or in the subject's body to monitor and transmit to the system's controller real time indicia of the subject's body temperature. The user enters a target body temperature which is lower than the subject's current monitored body temperature and selects operation in a mode/sub-mode whereby combined endovascular and body surface heat exchange will occur. The system's controller then causes the system to circulate controlled-temperature heat exchange fluid(s) through both the heat exchange catheter and body surface heat exchanger to lower the body temperature monitored by the temperature sensor(s) to the target body temperature. Thereafter, the controller causes the system to further circulate controlled-temperature heat exchange fluid(s) through both the heat exchange catheter and body surface heat exchanger as needed to maintain the monitored body temperature at (or within a predetermined range of) the target body temperature for a desired period of time. This technique may be used to induce and maintain a desired degree of hypothermia (e.g., a lowered body temperature in the range of 34.5-36.5 degrees C. or 32-36.5 degrees C. or less than 37 degrees C.) or to restore and maintain normothermia in a subject who is initially febrile.

In alternative embodiments, a portable body surface heat exchange device may be utilized during patient transport, prior to insertion of a heat exchange catheter into a subject's vasculature. For example, one or more body surface heat exchange device(s) may be positioned on one or more body surface(s) of the subject in the back of an ambulance or other emergency response vehicle to initiate cooling. Upon arrival at a hospital, the portable body surface heat exchange device may be coupled to an endovascular system, such that heat exchange fluid(s) can be circulated through both a heat exchange catheter and the body surface heat exchanger simultaneously to continue cooling and lower the body temperature. Alternatively, the portable body surface heat exchange device may be removed and another combined (endovascular+surface) heat exchange system as described herein may be used to continue cooling. At a later point in time, e.g., at the commencement of surgery, the one or more body surface heat exchange devices may be removed, and cooling performed solely using the endovascular heat exchange catheter.

Example 2

Rapid Induction of Hypothermia by Simultaneous Endovascular and Body Surface Heat Exchange Followed by Hypothermia Maintenance by Only Endovascular Heat Exchange In this example, a heat exchange system as described herein is used to rapidly induce and maintain therapeutic hypothermia in a human or other mammalian animal subject who is initially normothermic. A heat exchange catheter is inserted into the subject's vasculature (e.g., into the inferior vena cava or other suitable blood vessel) and one or more body surface heat exchange device(s) is/are positioned on one or more body surface(s) of the subject. A body temperature sensor is placed on or in the subject's body to monitor and transmit to the system's controller real time indicia of the subject's body temperature. The user enters a target hypothermic body temperature (e.g., less than 37 degrees C.) and selects operation in a mode/sub-mode whereby combined endovascular and body surface heat exchange will occur. The system's controller then causes the system to circulate controlled-temperature heat exchange fluid(s) through both the heat exchange catheter and body surface heat exchanger to lower the body temperature monitored by the temperature sensor(s) to the target hypothermic temperature. Thereafter, the user (manually) or the controller (automatically) may cause the system to shift to a mode and sub-mode wherein controlled-temperature heat exchange fluid(s) continue to circulate only through the endovascular heat exchange catheter as needed to maintain the monitored body temperature at (or within a predetermined range of) the target hypothermic body temperature for a desired period of time. At this stage, the body surface heat exchange device(s) may be disconnected and/or removed from the subject's body. This technique may be used to effect speedy induction of therapeutic hypothermia in subject's who are suffering an acute event that may benefit from rapid induction of hypothermia, for example an ischemic or traumatic event such as acute myocardial infarction, embolic stroke, traumatic brain or spinal cord injury, multiple organ trauma or failure, etc. The initial use of body surface heat exchange in combination with endovascular heat exchange enhances the rapidity with which the desired level of hypothermia may be induced. Thereafter, cessation of use of the body surface heat exchange device(s) while using the endovascular heat exchange catheter to maintain the induced hypothermia may allow for removal of the body surface heat exchange device(s) thereby fully exposing the subject's body surfaces as may be important for performance of needed interventional or surgical procedures or other indicated diagnostic or therapeutic endeavors.

Example 3

Hypothermia Induction with Subsequent Deterrence of Discomfort and/or Shivering Using Combined Endovascular and Body Surface Heat Exchange In this example, a heat exchange system as described herein is used to rapidly induce and maintain moderate to deep hypothermia in a human or other mammalian animal subject while providing some warming of the subject's body surface (e.g., the skin) to deter discomfort and/or shivering. A heat exchange catheter is inserted into the subject's vasculature (e.g., into the inferior vena cava or other suitable blood vessel) and one or more body surface heat exchange device(s) is/are positioned on one or more body surface(s) of the subject. A body temperature sensor is placed on or in the subject's body to monitor and transmit to the system's controller real time indicia of the subject's body temperature. The user enters a target hypothermic body temperature (e.g., 32-36.0 degrees C. or less than 37 degrees C.) and selects operation in a mode/sub-mode whereby combined endovascular and body surface heat exchange will occur. The system's controller then causes the system to circulate controlled-temperature heat exchange fluid(s) through both the heat exchange catheter and body surface heat exchanger to rapidly lower the body temperature for an initial period. Thereafter, for a subsequent period, the controller will cause the body surface heat exchange device(s) to apply warming to the subject's body surface while the endovascular heat exchange catheter continues to lower the core body temperature to the target hypothermic temperature and to thereafter maintain the core body temperature at or within a permitted variation range of that target hypothermic body temperature. Such shifting of the body surface heat exchange device(s) from cooling to warming may deter discomfort or the onset of a physiological shivering response as the subject's core body temperature continues to lower. Shifting of the body surface heat exchange device(s) from cooling to warming may be effected manually by the user or the system's controller may be programmed to cause such sift from surface cooling to surface warming to occur in response to the attainment of an initial amount of body temperature lowering (e.g., initial lowering of the body temperature to a temperature that is near the threshold for occurrence of shivering) or upon sensing of some predetermined event such as a change in a physiological variable or occurrence of a predetermined symptom (e.g., the onset of significant cold-induced discomfort or pre-shivering symptoms). In some embodiments, one or more sensor(s) may sense the occurrence of the event that causes this shift from surface cooling to surface warming. For example, copending U.S. patent application Ser. No. 14/783,912 entitled Detecting and Responding to Preshivering, the entire disclosure of which is expressly incorporated herein by reference, describes sensors and methods which may be used with the systems and devices described herein to sense when a shivering response is likely to occur but has not yet fully or actually commenced. Also, U.S. Pat. No. 8,475,509 (Dae) entitled Devices and Methods for Using Endovascular Cooling to Treat Septic Shock and Other Disorders, the entire disclosure of which is also expressly incorporated herein by reference, describes sensors and methods that may be used with the systems and devices described herein to detect other changes in a physiological variable or occurrence of a symptom which triggers the shift from surface cooling to surface warming. This technique may be used to optimize the rate of initial body temperature lowering (e.g., to provide for speedy induction of hypothermia in cases where time is of the essence) followed by the use of body surface warming to provide comfort or ward off untoward effects of the hypothermia.

Other heat exchange devices and systems are described in U.S. Pat. No. 7,070,612 (Collins et al.) entitled System And Method For Bringing Hypothermia Rapidly Onboard and United States Patent Application Publication No. 2015/0223972 (Dabrowiak, et al.) entitled Heat Exchange System For Patient Temperature Control With Multiple Coolant Chambers For Multiple Heat Exchange Modalities, the entire disclosure of each such patent and application being expressly incorporated herein by reference.

It is to be appreciated that, although the invention has been described hereabove with reference to certain examples or embodiments of the invention, various additions, deletions, alterations and modifications may be made to those described examples and embodiments without departing from the intended spirit and scope of the invention. For example, any elements, steps, members, components, compositions, reactants, parts or portions of one embodiment or example may be incorporated into or used with another embodiment or example, unless otherwise specified or unless doing so would render that embodiment or example unsuitable for its intended use. Also, where the steps of a method or process have been described or listed in a particular order, the order of such steps may be changed unless otherwise specified or unless doing so would render the method or process unsuitable for its intended purpose. Additionally, the elements, steps, members, components, compositions, reactants, parts or portions of any invention or example described herein may optionally exist or be utilized in the absence or substantial absence of any other element, step, member, component, composition, reactant, part or portion unless otherwise noted. All reasonable additions, deletions, modifications and alterations are to be considered equivalents of the described examples and embodiments and are to be included within the scope of the following claims.

What is claimed is:

1. A system for controlling body temperature of a subject, said system comprising:
    at least one endovascular heat exchange device;
    at least one body surface heat exchange device;
    at least one source of heat exchange fluid;
    at least one heater/cooler;
    at least one pumping apparatus;
    a user interface; and
    at least one controller which receives input from the user interface and is programmed to control operation of the system in alternate modes which comprise:
        a) a first mode wherein heated or cooled heat exchange fluid is circulated through the at least one endovascular heat exchange device in a first fluid loop;
        b) a second mode wherein heated or cooled heat exchange fluid is circulated through the at least one body surface heat exchange device in a second fluid loop; and
        c) a third mode wherein heated or cooled heat exchange fluid is circulated through both the at least one endovascular heat exchange device in the first fluid loop and the at least one body surface heat exchange device in the second fluid loop, the first fluid loop being separate from the second fluid loop;
    wherein said at least one controller is further programmed, and the user interface is further useable, such that when the third mode is selected the user may further select from a plurality of sub-modes in which the at least one endovascular heat exchange device and the at least one body surface heat exchange device are operable, the plurality of sub-modes comprising:
        i) a first sub-mode wherein the at least one endovascular heat exchange device and the at least one body surface heat exchange device simultaneously cool or warm;
        ii) a second sub-mode wherein a first one of the at least one endovascular heat exchange device and the at least one body surface heat exchange device cools while the other of the at least one endovascular heat exchange device and the at least one body surface heat exchange device warms; and
        iii) a third sub-mode wherein, for an initial period, the at least one endovascular heat exchange device and the at least one body surface heat exchange device simultaneously cool or warm and, for a subsequent period, one of the at least one endovascular heat exchange device and the at least one body surface heat exchange device cools while the other of the at least one endovascular heat exchange device and the at least one body surface heat exchange device warms; and
    wherein the at least one controller is configured to control a first valve of the first fluid loop to control an amount that the at least one endovascular heat exchange device cools or warms;
    wherein the at least one controller is configured to control a second valve of the second fluid loop to control an amount that the at least one body surface device cools or warms;
    wherein the system further comprises a physiological variable or symptom sensor configured to sense a predetermined change in a physiological variable or occurrence of a predetermined symptom; and
    wherein the initial period ends and the subsequent period begins when the physiological variable or symptom sensor senses the predetermined change in a physiological variable or occurrence of the predetermined symptom.

2. A system according to claim 1, wherein the at least one controller is programmed such that:
    during the initial period, the at least one controller causes the at least one endovascular heat exchange device to cool flowing blood of the subject and the at least one body surface heat exchange device cools a body surface of the subject; and
    during the subsequent period, the at least one controller causes the at least one endovascular heat exchange device to continue to cool flowing blood of the subject while the at least one body surface heat exchange device warms a body surface of the subject.

3. A system according to claim 1, wherein the system further comprises a temperature sensor device which measures or determines a core body temperature of the subject and wherein the initial period ends and the subsequent period begins when the determined core body temperature has reached a predetermined temperature.

4. A system according to claim 1, wherein the at least one endovascular heat exchange device comprises a heat exchange catheter through which heat exchange fluid circulates.

5. A system according to claim 1 wherein said at least one heater/cooler comprises a first heater/cooler for heating/cooling fluid for circulation through the endovascular heat exchange device and a second heater/cooler for heating/cooling heat exchange fluid for circulation through the at least one body surface heat exchange device.

6. A system according to claim 1 wherein said at least one heater/cooler comprises a first heater/cooler operative for heating/cooling fluid at one or more volume flow rates sufficient for circulation through the at least one endovascular heat exchange device and a second heater/cooler which augments the first heater/cooler to heat/cool fluid at one or more higher volume flow rates sufficient for circulation through the at least one body surface heat exchange device.

7. A system according to claim 1 wherein the at least one pumping apparatus comprises a first pumping apparatus which pumps heat exchange fluid at one or more volume flow rates suitable for circulation through the at least one endovascular heat exchange device and a second pumping apparatus which pumps heat exchange fluid at one or more volume flow rates suitable for circulation through the at least one body surface heat exchange device.

8. A system according to claim 1 wherein said at least one pumping apparatus comprises a first pump which pumps heat exchange fluid through the at least one endovascular heat exchange device and a second pump which is optionally useable, in combination with the first pump, to pump heat exchange fluid through the at least one body surface heat exchange device.

9. A system according to claim 1 wherein the heater/cooler is a first heater cooler, and wherein the at least one controller is programmed such that, when the at least one body surface heat exchange device is being used for warming and the at least one endovascular heal exchange device is being used for cooling, the at least one controller causes a second heater/cooler to use heat which exhausts from the heater/cooler to facilitate warming of the at least one body surface heat exchange device.

10. A system according to claim 9 wherein the at least one heater/cooler exhausts warm air and wherein the second heater/cooler comprises a conduit which circulates said warm air through the at least one body surface heat exchange device.

11. A system according to claim 9 wherein the at least one heater/cooler comprises a refrigeration device having a condenser which produces heat when the refrigeration device is being used to cool heat exchange fluid that circulates through the at least one endovascular heat exchange device and wherein heat from the condenser is used to warm air or heat exchange fluid that circulates through the at least one body surface heat exchange device.

12. A system according to claim 1 further comprising a second heater/cooler used for simultaneously heating or cooling heat exchange fluid circulated through the at least one endovascular heat exchange device as well as heat exchange fluid that circulates through the at least one body surface heat exchange device.

13. A system according to claim 12 wherein:
a first heat exchange fluid is circulated through the at least one endovascular heat exchange device and a second heat exchange fluid is circulated through the at least one body surface heat exchange device; and
a common extracorporeal heat exchange device that comprises a heat exchange cassette having a first flow path through which the first heat exchange fluid circulates and a second flow path through which the second heat exchange fluid circulates.

14. A system according to claim 13 wherein the first and second flow paths are constructed to prevent mixing or cross contamination between the first and second heat exchange fluids.

15. A system according to claim 14 wherein the first and second flow paths are separated by a polymer film.

16. A system according to claim 1 wherein the at least one pumping apparatus comprises a variable volume flow rate pumping apparatus configured to alternately pump heat exchange fluid at a plurality of volume flow rates suitable for use during operation of the system in any of said first, second or third modes.

17. A system according to claim 16 wherein the variable volume flow rate pumping device comprises a variable volume flow rate peristaltic pump including a first channel sized for pumping heat exchange fluid at a volume flow rate for circulation through the endovascular heat exchange device and including a second channel sized for separately pumping heat exchange fluid at a second volume flow rate for circulation through the at least one body surface heat exchange device.

18. A system according to claim 17 wherein the first channel comprises a race and/or tubing of a first size and the second channel comprises a race and/or tubing of a second size.

19. A system according to claim 17 wherein the variable volume flow rate peristaltic pump comprises a compressor which is operable to cause peristaltic compression of tubing of the first channel at a first compression and compression of tubing of the second channel at a second compression that is different than the first compression or tubing of both the first and second channels at a same compression.

20. A system according to claim 17 wherein the variable volume flow rate peristaltic pump comprises a plurality of compressors which are operable individually or in combination to alternately cause peristaltic compression of a) tubing of the first channel or b) tubing of the second channel or c) tubing of both the first and second channels.

21. A system according to claim 1 wherein the predetermined change in a physiological variable or occurrence of a predetermined symptom indicates that a shivering response has begun or is likely to begin as cooling of a core body temperature of the subject continues.

* * * * *